United States Patent
Shanthakumar et al.

(10) Patent No.: US 10,646,192 B2
(45) Date of Patent: May 12, 2020

(54) PEAK SHAVE ENABLED COMPUTED TOMOGRAPHY SYSTEM WITH BUILT-IN UNINTERRUPTIBLE POWER SUPPLY AND STABILIZER

(71) Applicant: General Electric Company, Schenectady, NY (US)

(72) Inventors: Shashanka Jain Belur Shanthakumar, Bengaluru (IN); Anbu Aras Arunachalam, Bengaluru (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 246 days.

(21) Appl. No.: 15/463,237

(22) Filed: Mar. 20, 2017

(65) Prior Publication Data
US 2018/0263591 A1    Sep. 20, 2018

(51) Int. Cl.
*A61B 6/00*    (2006.01)
*H02J 9/06*    (2006.01)
(Continued)

(52) U.S. Cl.
CPC .............. *A61B 6/56* (2013.01); *A61B 6/032* (2013.01); *H02J 3/32* (2013.01); *H02J 7/0021* (2013.01);
(Continued)

(58) Field of Classification Search
CPC .. H02J 3/32; H02J 7/0021; H02J 9/061; H02J 9/062; A61B 6/56
See application file for complete search history.

(56) References Cited

U.S. PATENT DOCUMENTS 5,226,064 A * 7/1993 Yahata ............... H05G 1/10
378/101
5,808,376 A * 9/1998 Gordon ............... G01T 1/175
307/64
(Continued)

FOREIGN PATENT DOCUMENTS

EP     3079038 A2    10/2016

OTHER PUBLICATIONS

International Search Report and Written Opinion for corresponding PCT application PCT/US2018/021450 dated May 7, 2018; 12 pages.

*Primary Examiner* — David J Makiya
*Assistant Examiner* — Soorena Kefayati
(74) *Attorney, Agent, or Firm* — Fletcher Yoder, P.C.

(57) ABSTRACT

A computed tomography (CT) scanning apparatus is provided. The CT scanning apparatus includes an energy storage component disposed in a stationary portion of the CT scanning apparatus, wherein the energy storage component is configured to receive electrical power from an external source and to store the electrical power. The CT scanning apparatus also includes an energy storage management system coupled to the energy storage component and configured to regulate both storage of the electrical power on the energy storage component and utilization of the electrical power stored on the energy storage component by the CT scanning apparatus. The energy storage component is configured to serve as an uninterruptible power supply (UPS) for the CT scanning apparatus and to provide peak power shaving during peak power operation of the CT scanning apparatus.

3 Claims, 8 Drawing Sheets

(51) Int. Cl.
   *A61B 6/03* (2006.01)
   *H02J 3/32* (2006.01)
   *H02J 7/00* (2006.01)

(52) U.S. Cl.
   CPC .............. *H02J 9/061* (2013.01); *H02J 9/062* (2013.01); *A61B 6/03* (2013.01)

(56) References Cited

U.S. PATENT DOCUMENTS

| | | | | |
|---|---|---|---|---|
| 5,946,208 A * | 8/1999 | Yamamoto | | A61B 6/488 363/132 |
| 8,218,726 B2 * | 7/2012 | Bressel | | A61B 6/032 378/103 |
| 8,379,797 B2 * | 2/2013 | Abenaim | | A61B 6/027 378/103 |
| 9,737,273 B2 * | 8/2017 | Gregerson | | A61B 6/035 |
| 2002/0050809 A1 * | 5/2002 | Uchida | | H02J 1/04 320/149 |
| 2004/0150371 A1 * | 8/2004 | Mount | | H02J 9/062 320/137 |
| 2005/0028014 A1 * | 2/2005 | Allred | | H02J 3/14 713/300 |
| 2006/0178579 A1 * | 8/2006 | Haynes | | A61B 8/08 600/437 |
| 2007/0253540 A1 * | 11/2007 | Anderton | | A61B 6/4405 378/199 |
| 2008/0112537 A1 * | 5/2008 | Katcha | | A61B 6/032 378/102 |
| 2010/0187430 A1 * | 7/2010 | Yoshimuta | | A61B 6/032 250/370.09 |
| 2010/0188875 A1 * | 7/2010 | Kalms | | H02J 1/06 363/34 |
| 2010/0200765 A1 * | 8/2010 | Nishino | | A61B 6/4233 250/395 |
| 2011/0122995 A1 * | 5/2011 | Ferro, Jr. | | A61B 6/4429 378/62 |
| 2011/0142203 A1 * | 6/2011 | Morton | | G01V 5/0008 378/98.2 |
| 2011/0175451 A1 * | 7/2011 | Moon | | H02J 9/062 307/66 |
| 2012/0027161 A1 * | 2/2012 | Abenaim | | A61B 6/027 378/4 |
| 2012/0326504 A1 * | 12/2012 | Ballantine | | H02J 3/006 307/24 |
| 2014/0070812 A1 * | 3/2014 | Yokoi | | A61B 6/032 378/4 |
| 2015/0036786 A1 * | 2/2015 | Katcha | | A61B 6/56 378/4 |
| 2015/0085969 A1 * | 3/2015 | Mekonnen | | H05G 1/10 378/4 |
| 2016/0233692 A1 * | 8/2016 | Hwang | | H02J 7/0021 |
| 2016/0285267 A1 * | 9/2016 | Stone | | G05B 15/02 |
| 2017/0047764 A1 * | 2/2017 | Lee | | H04B 1/3888 |
| 2017/0104350 A1 * | 4/2017 | Luerkens | | H01M 10/4207 |
| 2019/0044336 A1 * | 2/2019 | Wagner | | H02J 9/061 |

* cited by examiner

PEAK SHAVE ENABLED COMPUTED TOMOGRAPHY SYSTEM WITH BUILT-IN UNINTERRUPTIBLE POWER SUPPLY AND STABILIZER

BACKGROUND

The subject matter disclosed herein relates to computed tomography (CT) imaging systems or any X-ray system and, more particularly, to CT imaging systems configured to peak shave and/or having a built-in uninterruptible power supply (UPS) and stabilizer.

Medical CT systems utilize a large amount of power (e.g., peak power) for a short period of time (e.g., during emission of X-rays from the X-ray tube). Usually, a three-phase power source is utilized because the amount of electrical power needed during peak power operation by the CT system cannot be provided by a standard single phase power source. However, certain portions of the world do not have accessible three-phase power available and/or have to invest significant costs in to providing a suitable power infrastructure. In certain embodiments, an external UPS may be utilized to meet the peak power needs of the CT system. However, these external UPS systems may take up large amounts of space and be expensive. Therefore, there is a need for a CT system with improved power requirements.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, a computed tomography (CT) scanning apparatus is provided. The CT scanning apparatus includes an energy storage component disposed in a stationary portion of the CT scanning apparatus, wherein the energy storage component is configured to receive electrical power from an external source and to store the electrical power. The CT scanning apparatus also includes an energy storage management system coupled to the energy storage component and configured to regulate both storage of the electrical power on the energy storage component and utilization of the electrical power stored on the energy storage component by the CT scanning apparatus. The energy storage component is configured to serve as an uninterruptible power supply (UPS) for the CT scanning apparatus and to provide peak power shaving during peak power operation of the CT scanning apparatus.

In accordance with a second embodiment, a computed tomography (CT) scanning apparatus is provided. The CT scanning apparatus includes a first energy storage component and a second energy storage component separate from the first energy storage component, wherein the first and second energy storage components are disposed in a stationary portion of the CT scanning apparatus, wherein the first and second energy storage components are configured to receive electrical power from an external source and to store the electrical power. The CT scanning apparatus also includes an energy storage management system coupled to the first and second energy storage components and configured to regulate both storage of the electrical power on the first and second energy storage components and utilization of the electrical power stored on the energy storage components by the CT scanning apparatus. The first energy storage component is configured to serve as an uninterruptible power supply (UPS) for the CT scanning apparatus and the second energy storage component is configured to provide peak power shaving during peak power operation of the CT scanning apparatus.

In accordance with a third embodiment, a power distribution unit for a computed tomography (CT) scanning apparatus is provided. The power distribution unit includes multiple batteries stacked in series, wherein the multiple batteries are configured to receive electrical power from an external source and to store the electrical power. The power distribution unit also includes a battery charger and control circuitry coupled to the multiple batteries and configured to regulate both storage of the electrical power on the multiple batteries and utilization of the electrical power stored on the multiple batteries by the CT scanning apparatus. The multiple batteries are configured to serve as an uninterruptible power supply (UPS) for the CT scanning apparatus and to provide peak power shaving during peak power operation of the CT scanning apparatus, and the power distribution unit is configured to be disposed in a stationary portion of the CT scanning apparatus.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Systems and methods of the present disclosure are provided that relate to minimizing the power requirements of medical imaging systems (e.g., computed tomography (CT) system) and/or reducing costs associated with meeting the power requirements. In certain embodiments, the CT scanning apparatus may include a power distribution unit (PDU) configured to perform peak shaving (e.g., peak power shaving) to reduce the power requirements of the CT system. For example, the PDU (e.g., via control circuitry) during an imaging scan may turn off power to a battery charger during acceleration of a gantry of the CT scanning apparatus and then subsequently turn on power to the battery charger during emission of X-rays from the X-ray source or tube. In certain embodiments, the CT scanning apparatus may include an in-built (e.g., disposed within a stationary portion of the CT scanning apparatus) UPS and stabilizer. In certain embodiments, separate energy storage components may be utilized for providing power to the CT scanning apparatus (e.g., during peak power). In certain embodiments, a single energy storage component (e.g., a plurality of batteries stacked in series) may be utilized for both peak shaving and providing the UPS. Depending on a particular parameter (e.g., charge status of the energy storage component, time, type of scan, etc.), a particular mode of the UPS may be utilized (full UPS mode, partial UPS mode, console UPS mode) to provide a different amount or percentage of power (e.g., backup power) to the CT scanning apparatus. These various embodiments enable the CT scanning apparatus to reduce power requirements to enable the CT scanning apparatus to operate with single phase power sources, while reducing the costs (e.g., for power usage, power infrastructure, etc.) associated within the utilization of the CT scanning apparatus.

Although the following embodiments are discussed in terms of a CT imaging system or scanner, the embodiments may also be utilized with other imaging systems (e.g., PET, CT/PET, SPECT, nuclear CT, etc.). With the preceding in mind and referring to FIG. 1, a CT imaging system 10 is shown, by way of example. The CT imaging system includes a gantry 12. The gantry 12 has an X-ray source 14 that projects a beam of X-rays 16 toward a detector assembly 15 on the opposite side of the gantry 12. The detector assembly 15 includes a collimator assembly 18, a plurality of detector modules 20, and data acquisition systems (DAS) 32. The plurality of detector modules 20 detect the projected X-rays that pass through a patient 22, and DAS 32 converts the data to digital signals for subsequent processing. Each detector module 20 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 24 so as to collect attenuation data from a multitude of view angles relative to the imaged volume.

Figure 1:
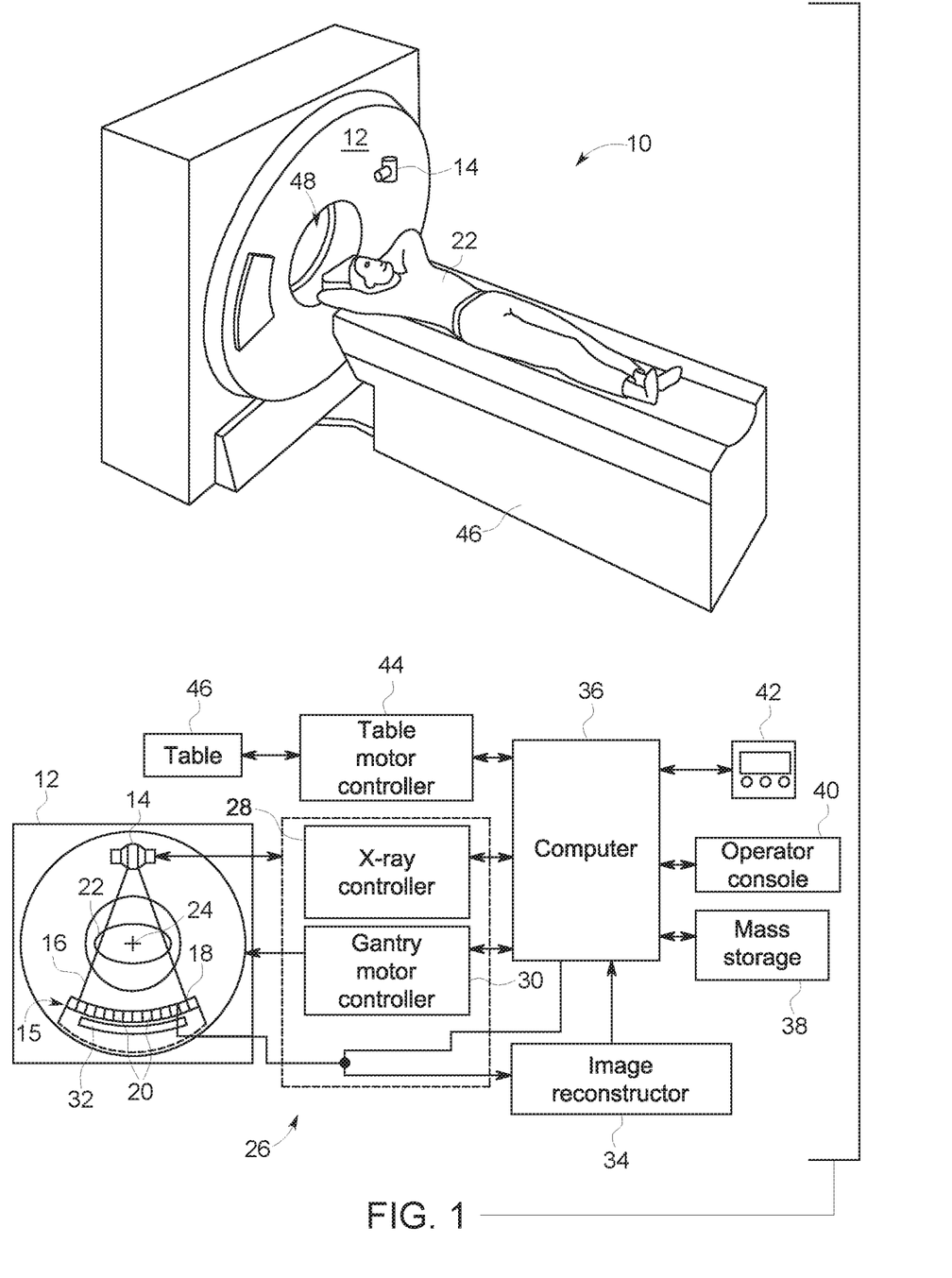
FIG. 1 is a combined pictorial view and block diagram of embodiment of a computed tomography (CT) imaging system as discussed herein.

Rotation of gantry 12 and the operation of X-ray source 14 are governed by a control mechanism 26 of CT system 10. Control mechanism 26 includes an X-ray controller 28 that provides power and timing signals to an X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 to position patient 22 and gantry 12. Particularly, table 46 moves (e.g., extends) portions of patient 22 on the patient support through a gantry opening or bore 48.

Figure 2:
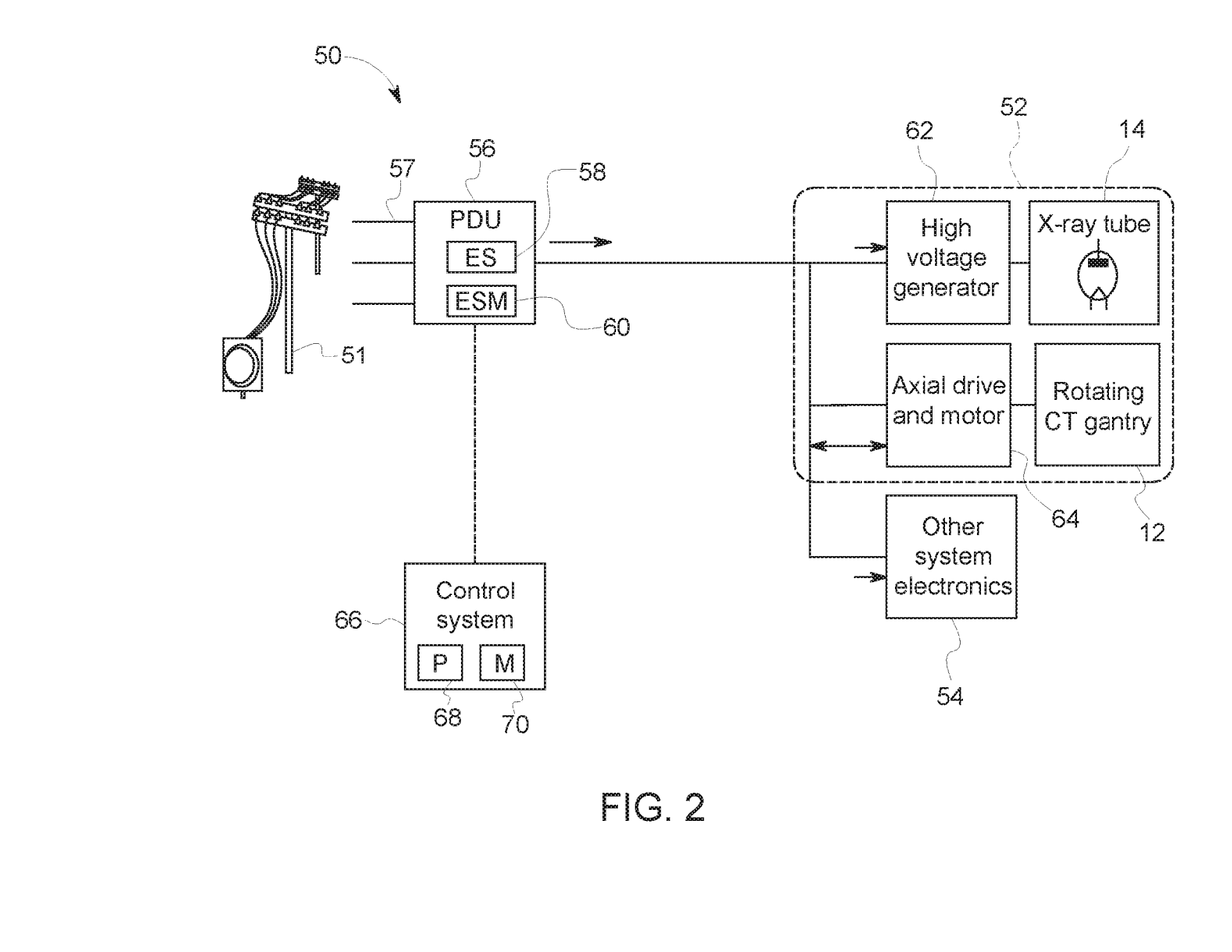
FIG. 2 is a block diagram of an embodiment of a power supply system having an uninterruptable power supply (UPS) and/or peak shaving for a medical imaging load.

FIG. 2 is a power supply system 50 that provides power to one or more medical imaging loads 52 (e.g., CT imaging system 10 of FIG. 1) and/or other electronics 54 (e.g., computer 36, console 40, and/or display 42 for CT imaging system 10). A main alternating current (AC) power source may provide power (e.g., single phase or polyphase AC power such as 3-phase AC power) via an AC power line 51 to a power distribution unit (PDU) 56 via an AC input 57 (e.g., single phase or 3-phase power plug). The PDU 56 may convert the AC power to DC power and provide the DC power to the medical imaging loads 52 and/or other electronics 54. In certain embodiments, the PDU 56 also provides AC power to the medical imaging loads 52 and/or other electronics 54. The PDU 56 is disposed in a stationary portion of the CT imaging scanner of the system 10. The PDU 56 may transmit power from the stationary portion to the rotating portion of the CT imaging scanner of the system 10 via a slip ring or wirelessly. In certain embodiments, the system 10 may utilize intelligent monitoring reporting of different parameters of the power supply system 50 (e.g., PDU 56). These parameters may include input voltage, input current, battery voltage charge current, inverter AC voltage, inverter AC current, heat sink temperature, all board rail voltages, and other parameters. These parameters may be communicated (e.g., wired or wirelessly) to the host computer 36 and/or console 40 from the PDU 56 via a communication interface (e.g., serial, controller area network, Ethernet, etc.).

The PDU 56 includes an energy storage system 58 configured to store electrical power provided by the AC power line 51. In certain embodiments, the energy storage system 58 includes one or more energy storage components. For example, in certain embodiments, the energy storage system 58 may include a first energy storage component to serve as an UPS (e.g., internal UPS) and a second energy storage component that enables peak shaving (e.g., during peak power operation of the CT imaging system 10). In other embodiments, the energy storage system 58 that includes a single energy storage component that is utilized as an UPS and during peak shaving. In certain embodiments, the energy storage components may include a plurality of batteries stacked in series. In some embodiments, the PDU 56 may be coupled to an external UPS. Various topologies of the UPS may be utilized to provide power (e.g., backup power) in situations where there is not enough power to enable peak power operation of the CT imaging system 10 (e.g., power outages and disturbances, absence of 3-phase power, etc.). The topologies of AC based UPS systems may include off-line, online, line-interactive and series-parallel line-interactive topologies.

The PDU 56 also includes an energy storage management system 60 configured to manage or control the storage on and distribution of power from the energy storage system 58. In certain embodiments, the energy storage management system 60 may include a battery charger and control circuitry. In certain embodiments, the energy storage management system 60 is configured to enable storage of the electrical power on the energy storage system 58 (e.g., batteries) without pre-regulation of the electrical power. In certain embodiments, the energy storage management system 60 is configured to perform peak shaving utilizing the energy storage system 58 (e.g., during an imaging scan) by turning off power provided to the battery charger during acceleration of the gantry 12 and subsequently turning on power to the battery charger during emissions of X-rays from the X-ray source 14 (e.g., X-ray tube). In certain embodiments, the energy storage management system 60 is configured to monitor a life of the batteries of the energy storage system 58 and to provide an indication that the batteries are nearing an end of the life via a user interface. For example, the energy storage management system 60 may monitor the equivalent series resistance (ESR) of the batteries and compared it to a threshold (e.g., maximum allowable ESR value). In certain embodiments, the energy storage management system 60 may determine a charge status of the batteries and/or determine whether an imaging scan can be conducted. For example, the energy storage management system 60 may utilize the batteries for the peak power operation when there is enough charge in the batteries or, if there is not enough charge, wait to utilize the batteries for peak power operation when there is enough charge. In certain embodiments, the energy storage management system 60 may select a UPS mode of operation for utilization of the UPS (e.g., during peak power operation) based on a parameter (e.g., charge status of batteries, type of imaging scan, time, etc.). For example, the energy storage management system 60 may select from a full UPS mode (e.g., batteries provide all of the power to the CT scanning apparatus during peak power operation), a partial UPS mode (e.g., batteries provide power only to a portion of the peak power operation that does not involve generating X-rays from the X-ray source 14), and a console UPS mode (e.g., batteries provide power only to the other system electronics 54 (e.g., operator console 40, computer 36, etc.)).

While one or more medical imaging loads 52 are described below with respect to loads for a computed tomography (CT) system, it will be appreciated that embodiments are applicable for use with other imaging configurations. The one or more medical imaging loads 52 may include a high voltage generator 62 coupled to the PDU 56. The high voltage generator 62 may provide power to an X-ray tube 14, of the computed tomography (CT) imaging system 10. The X-ray tube 14 may emit X-ray beams toward a subject or object, such as a patient. The beam, after being attenuated by the subject, impinges upon an array of radiation detector. The intensity of the attenuated beam radiation received at the detector array may be dependent upon the attenuation of the X-ray beam by the subject. Each detector element of the detector array produces a separate electrical signal indicative of the attenuated beam received by each detector element. The electrical signals are transmitted to a data processing system for analysis which produces an image. Further, the X-ray source and the detector array may be rotated, via an axial drive and motor 64, about the gantry 12 within an imaging plane and around the subject or object. When the gantry 12 is rotated, it converts the power from the PDU 56 to rotational kinetic energy via the motor 64.

The PDU 56 may be controlled by a control system 66 having a FPGA or processor 68 or multiple FPGA or multiple processors and memory 70. In certain embodiments, the control system 66 is part of the PDU 56 (e.g., energy storage management system 60). The processor 68 may be operatively coupled to the memory 70 to execute instructions for carrying out the presently disclosed techniques. These instructions may be encoded in programs or code stored in a tangible non-transitory computer-readable medium, such as the memory 70 and/or other storage. The processor 68 may be a general purpose processor (e.g., processor of a desktop/laptop computer), system-on-chip (SoC) device, or application-specific integrated circuit, or some other processor configuration. The memory 70, in the embodiment, includes a computer readable medium, such as, without limitation, a hard disk drive, a solid state drive, diskette, flash drive, a compact disc, a digital video disc, random access memory (RAM), and/or any suitable storage device that enables the processor 68 to store, retrieve, and/or execute instructions and/or data. The memory 70 may include one or more local and/or remote storage devices. The processor 66 may control components of the PDU 56 (e.g., charger, batteries, etc.) to provide power to the one or more medical imaging loads 52.

Figure 3:
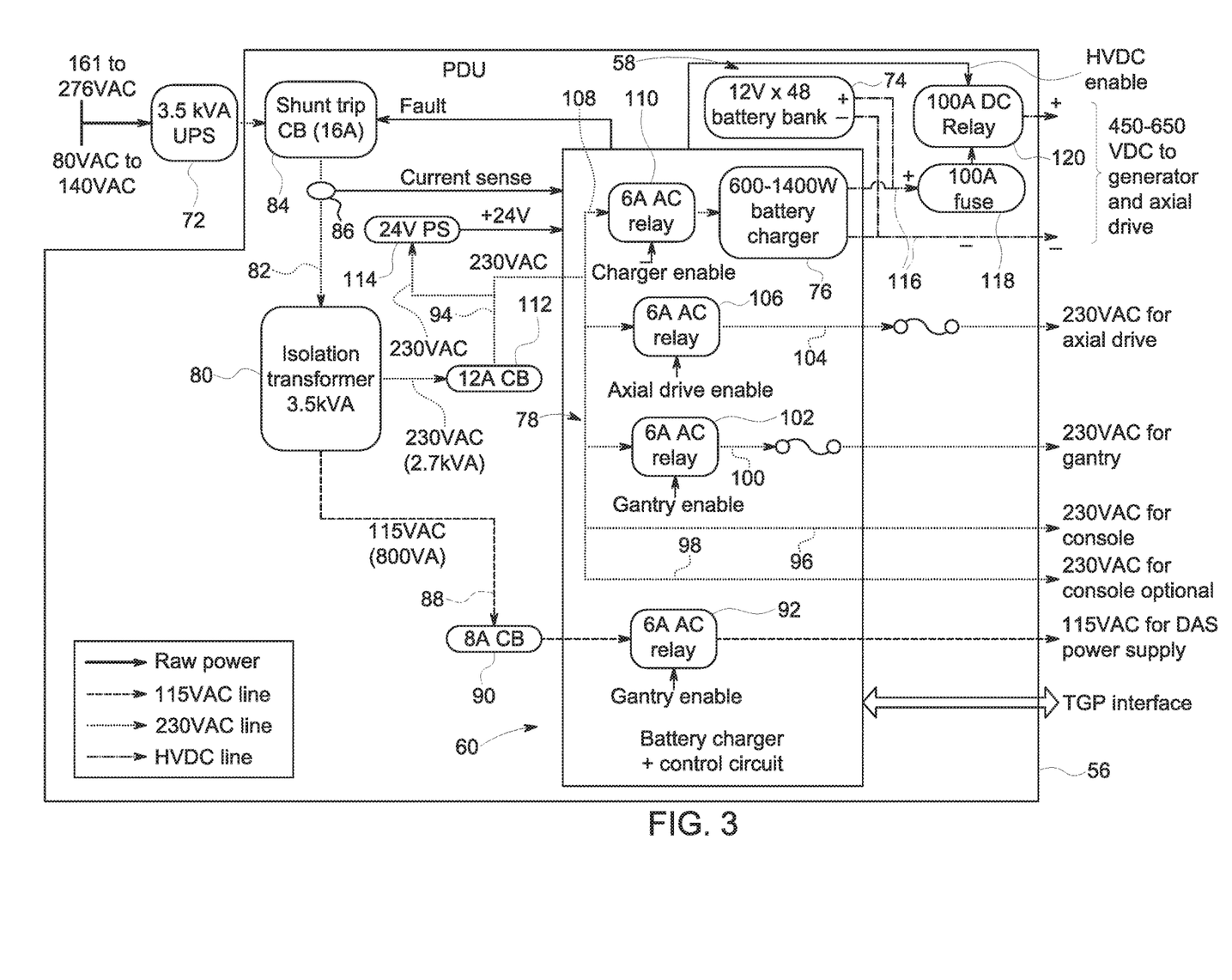
FIG. 3 is a schematic diagram of an embodiment of a power distribution unit (PDU) of FIG. 2 (e.g., coupled to an external UPS)
Figure 4:
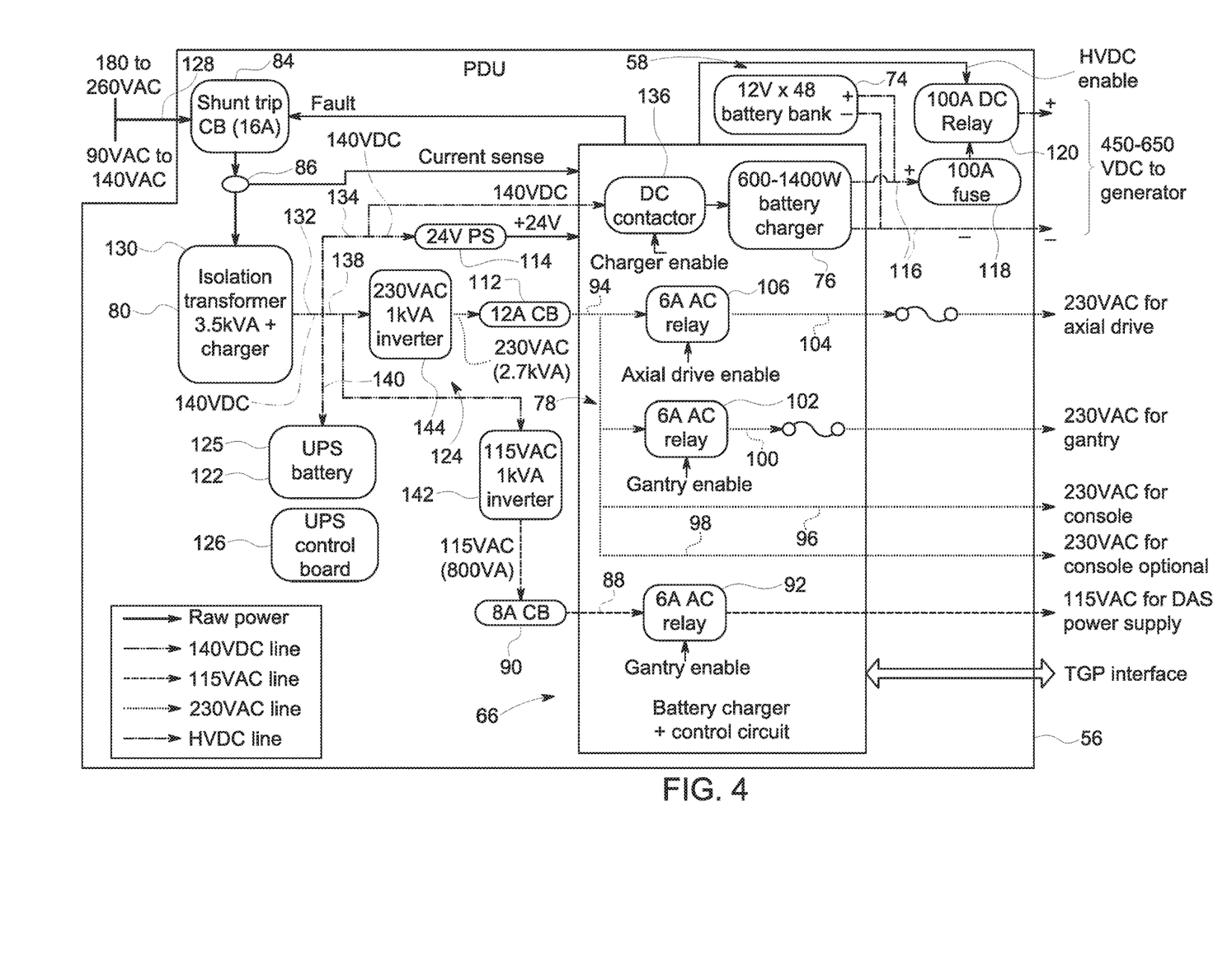
FIG. 4 is a schematic diagram of an embodiment of the PDU of FIG. 2 (e.g., having a built-in UPS and two separate energy storage elements)
Figure 5:
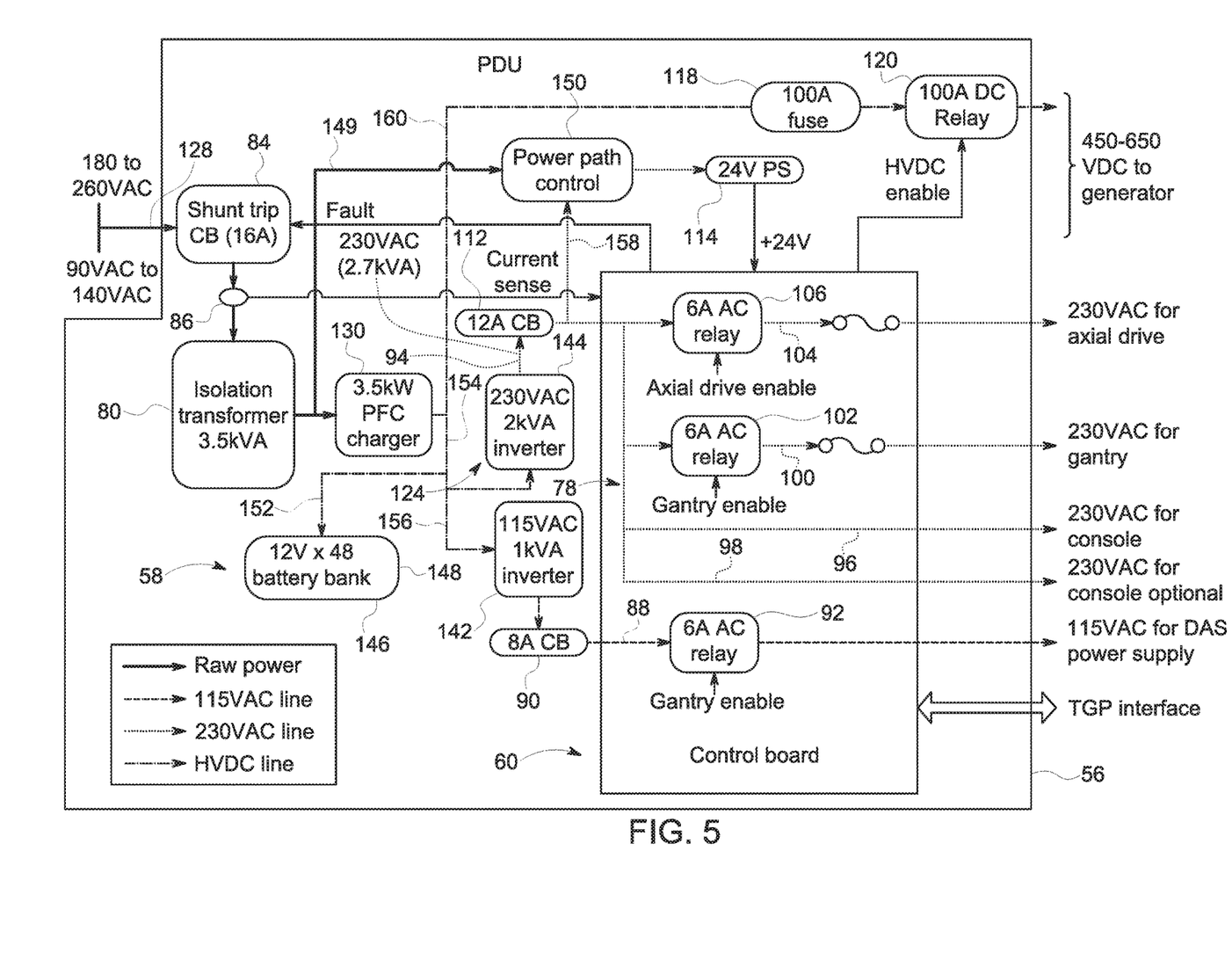
FIG. 5 is a schematic diagram of an embodiment of the PDU of FIG. 2 (e.g., having a single energy storage component for a UPS and peak shaving)

FIGS. 3-5 illustrate different embodiments of the PDU 56 for the CT imaging system 10 (e.g., typically having a power requirement of approximately 40 kVA) that provide universal voltage support and enable the system 10 to be operated at approximately 3.5 kVA when coupled to a single phase AC power source. Although illustrated coupled to a single-phase power supply, in certain embodiments, the PDU 56 in FIGS. 3-5 may be coupled to a polyphase power supply (e.g., 3-phase power supply). FIG. 3 is a schematic diagram of an embodiment of the PDU 56 of FIG. 2 (e.g., coupled to an external UPS 72). The PDU 56 includes the energy storage system 58 and the energy storage management system 60. The energy storage system 58 includes an energy storage component 74 that includes a plurality of batteries stacked in series. The stacking of the batteries in series avoids needing a pre-regulator. Although the number of batteries is depicted as 48, the number may vary so as long as the need for a pre-regulator is avoided. As described in greater detail below, the PDU 56 utilizes the energy storage component 74 for peak shaving (e.g., during peak power operation of the CT system 10). The energy storage management system 60 includes a battery charger 76 and control circuitry 78 (e.g., control board) that manages the distribution of power from the UPS 72 and the energy storage system 58. In certain embodiments, the energy storage management system 60 interfaces with a table gantry PDU control (TGP).

As depicted, the PDU 56 is coupled to the external UPS 72 (e.g., 3.5 kVA UPS). The UPS 72 is coupled to a single phase AC power source. In certain embodiments, the UPS 72 could be coupled to a polyphase power supply (e.g., 3-phase power supply). The UPS 72 provides electrical power to an isolation transformer 80 (e.g., 3.5 kVA isolation transformer) via line 82 (e.g., 230 VAC line). In certain embodiments, the isolation transformer 80 may include two windings on the input side. This enables the isolation transformer 80 to include different tapping options. For example, the isolation transformer 80 can have the windings coupled in series (e.g., for 180-260 VAC input) or in parallel (for 90-140 VAC input). A shunt trip circuit breaker 84 may be disposed along the line 82 between the UPS 72 and the transformer 80. The shunt trip circuit breaker 84 trips in the presence of a fault. In certain embodiments, a current sensor 86 may be disposed along the line 82 (e.g., between the shunt trip circuit breaker 84 and the isolation transformer 80).

The isolation transformer 80 provides AC power to the energy storage management system 60. In particular, a portion of the AC power (e.g., 800 VA) may be provided via line 88 (e.g., 115 VAC line) to the energy storage management system 60 and subsequently to a power supply for the DAS 32. In certain embodiments, a circuit breaker 90 and an AC relay 92 may be disposed along line 88 downstream of the transformer 80. The AC relay 92 is turned on (e.g., gantry enabled) when the gantry 12 is being utilized.

Another portion of the AC power (e.g., 2.7 kVA) may be provided via line 94 (e.g., 230 VAC line) to the energy storage management system 60. From energy storage management system 60 a portion of the AC power is provided to other system electronics 54 (e.g., computer 36, console 40, etc.) along one or more portions 96, 98 of line 94. Also, a portion of the AC power is provided to the gantry 12 along portion 100 of line 94. An AC relay 102 may be disposed along portion 100 that is turned on (e.g., gantry enabled) when the gantry 12 is being utilized. Further, a portion of the AC power is provided to the axial drive and motor 64 along portion 104 of line 94. An AC relay 106 may be disposed along portion 104 that is turned on (e.g., axial drive enabled) when the axial drive and motor 64 is being utilized. Even further, a portion of the AC power is provided to the battery charger 76 (e.g., 600-1400 W battery charger) along portion 108 of line 94. An AC relay 110 may be disposed along portion 108 upstream of the battery charger 76 that is turned (e.g., charger enabled) when the battery charger 76 is being utilized.

In certain embodiments, upstream of portions 96, 98, 100, 104, 108 and downstream of transformer 80, a circuit breaker 112 may be disposed along the line 94. In certain embodiments, upstream of portions 96, 98, 100, 104, 108 and downstream of transformer 80, the line 94 may be coupled to a power supply 114 (e.g., 24V power supply) which provides power to the energy storage management system 60.

The battery charger 76 is coupled to and provides power to the batteries 74. The batteries 74 and the battery charger 76 provide DC power (e.g., 450-650 VDC) to the generator 62 and the axial drive and rotor 64 along line 116. In certain embodiments, a fuse 118 and a DC relay 120 may be disposed (e.g., downstream of the batteries 74 and the battery charger 76) along the positive portion of line 116. The DC relay 120 is turned on (e.g., high voltage (HV) DC enabled) when high voltage DC power is provided to the generator 62.

FIG. 4 is a schematic diagram of an embodiment of the PDU 56 of FIG. 2 (e.g., having an internal or built-in UPS 122 and two separate energy storage elements). In general, the PDU 56 is as described in FIG. 3 except it includes the built-in UPS 122 (e.g., in the stationary portion of the CT scanner) with a wide range stabilizer 124 (e.g., wide range voltage stabilizer having a range of approximately 90-140 VAC and 180-260 VAC). The PDU 56 includes the energy storage system 58 and the energy storage management system 60. The energy storage system 58 includes the first energy storage component 74 that includes a plurality of batteries stacked in series. The stacking of the batteries in series avoids needing a pre-regulator. Although the number of batteries is depicted as 48, the number may vary so as long as the need for a pre-regulator is avoided. The energy storage system 58 also includes a second energy storage component 125 (i.e., UPS 122). The UPS 122 may also include a plurality of batteries. The UPS 122 may be coupled to and regulated by UPS control board 126. As described in greater detail below, the PDU 56 utilizes the energy storage component 74 for peak shaving (e.g., during peak power operation of the CT system 10). The PDU 56 utilizes the UPS 122 to provide power (e.g., backup power) during operation of the CT system 10 (e.g., peak power operation). The energy storage management system 60 includes a battery charger 76 and control circuitry 78 that manages the distribution of power from the first and second storage components 74 and 125 of the energy storage system 58. In certain embodiments, the battery charger 76 is power limited and may be configured to various input AC power levels (e.g., 3.5 kVA, 10 kVA, etc.) and intermittent peak currents can be provided with the battery or batteries. In certain embodiments, the energy storage management system 60 interfaces with a TGP.

As depicted, the PDU 56 is coupled to a single phase AC power source via line 128 that provides electrical power to the isolation transformer 80 (e.g., 3.5 kVA isolation transformer) and charger 130. In certain embodiments, the PDU 56 could be coupled to a polyphase power supply (e.g., 3-phase power supply). In certain embodiments, the isolation transformer 80 may include two windings on the input side. This enables the isolation transformer 80 to include different tapping options. For example, the isolation transformer 80 can have the windings coupled in series (e.g., for 180-260 VAC input) or in parallel (for 90-140 VAC input). The charger 130 provides DC power to the UPS 122 via portion 140 of line 132 (e.g., 140 VDC line). A shunt trip circuit breaker 84 may be disposed along the line 128 upstream of the transformer 80 and charger 130. The shunt trip circuit breaker 84 trips in the presence of a fault. In certain embodiments, the current sensor 86 may be disposed along the line 128 (e.g., between the shunt trip circuit breaker 84 and the isolation transformer 80/charger 130).

The isolation transformer 80 provides power to the battery charger 76 (e.g., 600-1400 W) via portion 134 of line 132. A DC contactor 136 may be disposed between the battery charger 76 and the isolation transformer 80. The DC contactor 136 is turned on (e.g., charger enabled) when the battery charger 76 is being utilized. The isolation transformer 80 also provides power to the power supply 114 (e.g., 24 V power supply) which provides power to the energy storage management system 60. The isolation transformer 80 further provides power to the wide range stabilizer 124. The stabilizer 124 includes a first inverter 142 (e.g., 115 VAC/1 kVA inverter) and a second inverter 144 (e.g., 230 VAC/1 kVA inverter) that converts the DC power to AC power that is provided to the energy storage management system 60. In particular, a portion of the AC power (e.g., 800 VA) may be provided via line 88 (e.g., 115 VAC line) to the energy storage management system 60 and subsequently to a power supply for the DAS 32. In certain embodiments, the inverters 142, 144 may include a single-phase or polyphase output configuration when needed. In certain embodiments, a circuit breaker 90 and an AC relay 92 may be disposed along line 88 downstream of the first inverter 142. The AC relay 92 is turned on (e.g., gantry enabled) when the gantry 12 is being utilized.

Another portion of the AC power (e.g., 2.7 kVA) may be provided via line 94 (e.g., 230 VAC line) to the energy storage management system 60. From energy storage management system 60, a portion of the AC power is provided to other system electronics 54 (e.g., computer 36, console 40, etc.) along one or more portions 96, 98 of line 94. Also, a portion of the AC power is provided to the gantry 12 along portion 100 of line 94. The AC relay 102 may be disposed along portion 100 that is turned on (e.g., gantry enabled) when the gantry 12 is being utilized. Further, a portion of the AC power is provided to the axial drive and motor 64 along portion 104 of line 94. The AC relay 106 may be disposed along portion 104 that is turned on (e.g., axial drive enabled) when the axial drive and motor 64 is being utilized. In certain embodiments, upstream of portions 98, 100, 104 and downstream of the second inverter 144, the circuit breaker 112 may be disposed along the line 94.

The battery charger 76 is coupled to and provides power to the batteries 74. The batteries 74 and the battery charger 76 provide DC power (e.g., 450-650 VDC) to the generator 62. In certain embodiments, the fuse 118 and the DC relay 120 may be disposed (e.g., downstream of the batteries 74 and the battery charger 76) along the positive portion of line 116. The DC relay 120 is turned on (e.g., HV DC enabled) when high voltage DC power is provided to the generator 62.

FIG. 5 is a schematic diagram of an embodiment of the PDU 56 of FIG. 2 (e.g., having a single energy storage component 146 for a UPS and peak shaving). In general, the PDU 56 is as described in FIG. 4 except the single energy storage component 146 is utilized for peak shaving (e.g., during peak power operation) and as UPS 148 (e.g., disposed in the stationary portion of the CT scanner). The PDU 56 includes the energy storage system 58 and the energy storage management system 60. The energy storage system 58 includes the single energy storage component 146 that includes a plurality of batteries stacked in series. The stacking of the batteries in series avoids needing a pre-regulator. Although the number of batteries is depicted as 48, the number may vary so as long as the need for a pre-regulator is avoided. As described in greater detail below, the PDU 56 utilizes the energy storage component 146 for peak shaving (e.g., during peak power operation of the CT system 10) and to provide power (e.g., backup power) during operation of the CT system 10 (e.g., peak power operation). The energy storage management system 60 includes control circuitry 78 that manages the distribution of power from the energy storage component 146 of the energy storage system 58. In certain embodiments, the energy storage management system 60 interfaces with a TGP.

As depicted, the PDU 56 is coupled to a single phase AC power source via line 128 that provides electrical power to the isolation transformer 80 (e.g., 3.5 kVA isolation transformer). In certain embodiments, the PDU 56 could be coupled to a polyphase power supply (e.g., 3-phase power supply). In certain embodiments, the isolation transformer 80 may include two windings on the input side. This enables the isolation transformer 80 to include different tapping options. For example, the isolation transformer 80 can have the windings coupled in series (e.g., for 180-260 VAC input) or in parallel (for 90-140 VAC input). The isolation transformer 80 provides power to the charger 130 (e.g., 3.5 kW power factor correction charger). A shunt trip circuit breaker 84 may be disposed along the line 128 upstream of the transformer 80 and charger 130. The shunt trip circuit breaker 84 trips in the presence of a fault. In certain embodiments, the current sensor 86 may be disposed along the line 128 (e.g., between the shunt trip circuit breaker 84 and the isolation transformer 80). The isolation transformer 80 provides power to a power path control 150 via portion 149 of line 128.

The charger 130 provides DC power along portion 152 of line 154 to the batteries 146. The charger 130 also provides DC power to the wide range stabilizer 124 via portion 156 of line 154. The stabilizer 124 includes the first inverter 142 (e.g., 115 VAC/1 kVA inverter) and the second inverter 144 (e.g., 230 VAC/1 kVA inverter) that converts the DC power to AC power that is provided to the energy storage management system 60. In particular, a portion of the AC power (e.g., 800 VA) may be provided via line 88 (e.g., 115 VAC line) to the energy storage management system 60 and subsequently to a power supply for the DAS 32. In certain embodiments, the inverters 142, 144 may include a single-phase or polyphase output configuration when needed. In certain embodiments, a circuit breaker 90 and an AC relay 92 may be disposed along line 88 downstream of the first inverter 142. The AC relay 92 is turned on (e.g., gantry enabled) when the gantry 12 is being utilized.

Another portion of the AC power (e.g., 2.7 kVA) may be provided via line 94 (e.g., 230 VAC line) to the energy storage management system 60. From energy storage management system 60, a portion of the AC power is provided to other system electronics 54 (e.g., computer 36, console 40, etc.) along one or more portions 96, 98 of line 94. Also, a portion of the AC power is provided to the gantry 12 along portion 100 of line 94. The AC relay 102 may be disposed along portion 100 that is turned on (e.g., gantry enabled) when the gantry 12 is being utilized. Further, a portion of the AC power is provided to the axial drive and motor 64 along portion 104 of line 94. The AC relay 106 may be disposed along portion 104 that is turned on (e.g., axial drive enabled) when the axial drive and motor 64 is being utilized. In certain embodiments, upstream of portions 98, 100, 104 and downstream of the second inverter 144, the circuit breaker 112 may be disposed along the line 94. Downstream of the circuit breaker 112 and upstream of AC relay 106, AC power may be provided to the power path control 150 via portion 158 of line 94. The power path control 150 provides AC power to the power supply 114 (e.g., 24 V power supply) which provides power to the energy storage management system 60. Power path can be implemented using a relay, a solid state relay, or MOSFETS.

The charger 130 and/or batteries 146 provide DC power (e.g., 450-650 VDC) to the generator 62 along portion 160 of line 154 (HVDC line). In certain embodiments, the fuse 118 and the DC relay 120 may be disposed (e.g., downstream of the batteries 74 and the battery charger 76) along the portion 160 of line 154. The DC relay 120 is turned on (e.g., HVDC enabled) when high voltage DC power is provided to the generator 62. In certain embodiments, the battery charger 76 is power limited and may be configured to various input AC power levels (e.g., 3.5 kVA, 10 kVA, etc.) and intermittent peak currents can be provided with the battery or batteries.

Figure 6:
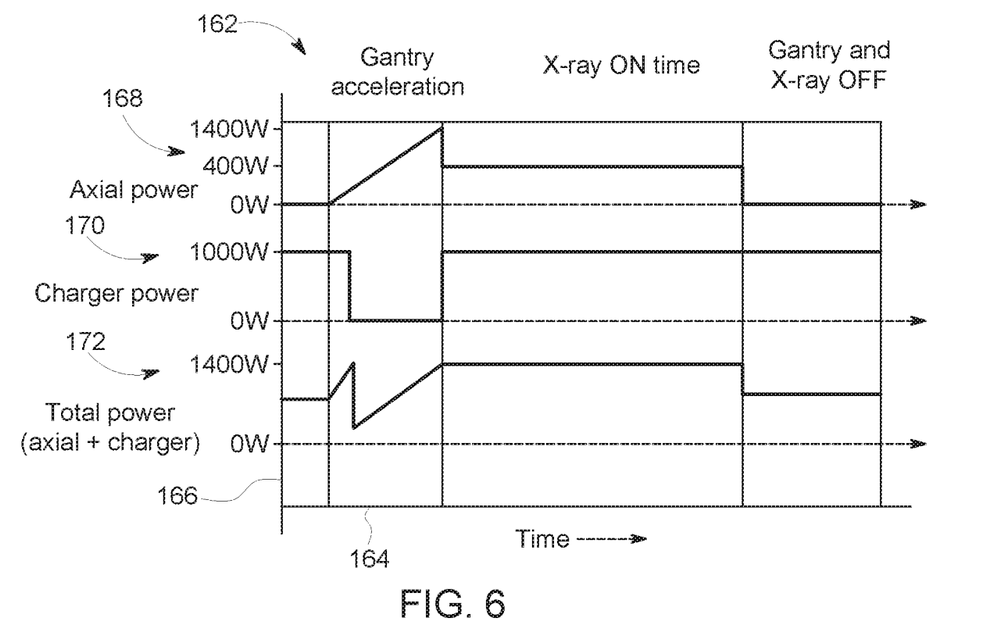
FIG. 6 is a graphical representation of an embodiment of how power requirements can be reduced during a scanning operation.

Besides utilizing an UPS and peak shaving to reduce the power requirements of CT imaging system 10 (e.g., from 40 kVA to 3.5 kVA) to enable the system 10 to be operated when coupled to a single phase AC power source, the PDU 56 (e.g., control circuitry 78 of the energy storage management system 60) may utilize various techniques to reduce the usage of power and, thus, the power requirements of the system 10. FIG. 6 is a graphical representation of an embodiment of how power requirements can be reduced during a scanning operation (e.g., with the PDU 56 of FIG. 3). FIG. 6 depicts a graph 162 having an X-axis 164 representing time and a Y-axis 166 representing power utilized (in W). The graph 162 represents the power utilized during a scanning operation (e.g., of the CT system 10) from beginning to end. The graph 162 is divided into three sections 168, 170, 172. Section 168 represents axial power (i.e., power provided to the axial drive and motor 64 of the CT system 10). Section 170 represents charger power (i.e., power provided to the battery charger of the energy storage management system 60). Section 172 represents total power (i.e., both axial and charger power). Prior to gantry acceleration, power (e.g., charger power) is only provided to the battery charger (e.g., 1000 W). During gantry acceleration, power (e.g., axial power) is provided to (and gradually increased) to the axial drive and motor 64 (e.g., up to 1400 W), while power (e.g., charger power) is no longer provided to the battery charger. Once emission of X-rays from the X-ray source 14 begin, axial power provided to the axial drive and motor 64 is decreased (e.g., 400 W), while providing charger power to the battery charger is resumed (e.g., 1000 W). After emission of X-rays is over and the gantry 12 is no longer rotating, axial power is no longer provided to the axial drive and motor 64, while charger power is still provided to the battery charger. As depicted in the graph 160, at no point during the scanning operation does the total power utilized by the battery charger and the axial drive and motor 64 exceed 1400 W. This enables the total power utilized by the CT system 10 during peak power operation to stay around 3000 to 3500 kW as the power utilized by the battery charger and the axial drive and motor 64 represents the greatest percentage of the power utilized by the system 10 (as opposed to the PDU 56, the gantry 14, etc.).

Figure 7:
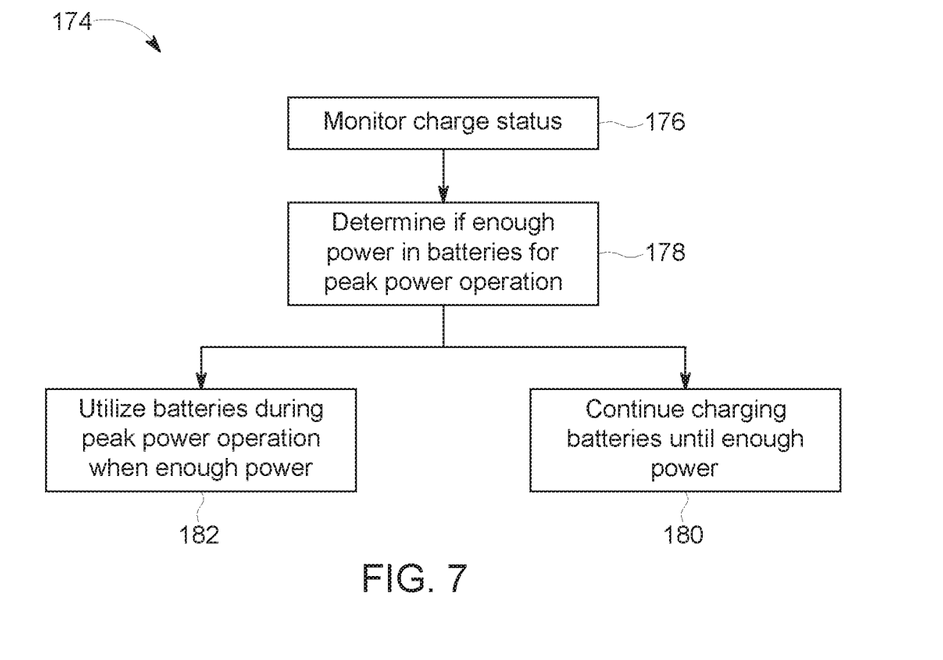
FIG. 7 is a flow diagram of an embodiment of a method for managing the utilization of power from an energy storage system.

FIG. 7 is a flow diagram of an embodiment of a method 174 for managing the utilization of power from the energy storage system of the PDU 56. One or more steps of the method 174 may be performed by the energy storage management system 60 (e.g., control circuitry 78) and/or the control system 66. One or more of the steps of the method 174 may be performed in a different order as depicted in FIG. 7 and/or performed simultaneously. The method 174 includes monitoring a charge status of a battery (or batteries) of an energy storage component (e.g., utilized for the UPS and/or peak shaving) of the PDU 56 (block 176). The method 174 also include determining if there is enough power (e.g., backup power) in battery or batteries of the energy storage component to utilize the CT system 10 (e.g., in a peak power operation such as an imaging scan) (block 178). If there is not enough power, the method 174 includes waiting to utilize the energy storage component and to continue charging the batteries until there is enough power (block 180). In certain embodiments, a user perceptible indication may be provided to indicate there is not enough power to perform the peak power operation and/or to suggest using a lower power image scan according to the charge status. If there is enough power, the method 174 includes utilizing the energy storage component during peak power operation (e.g., imaging scan) of the CT system 10 (block 182).

Figure 8:
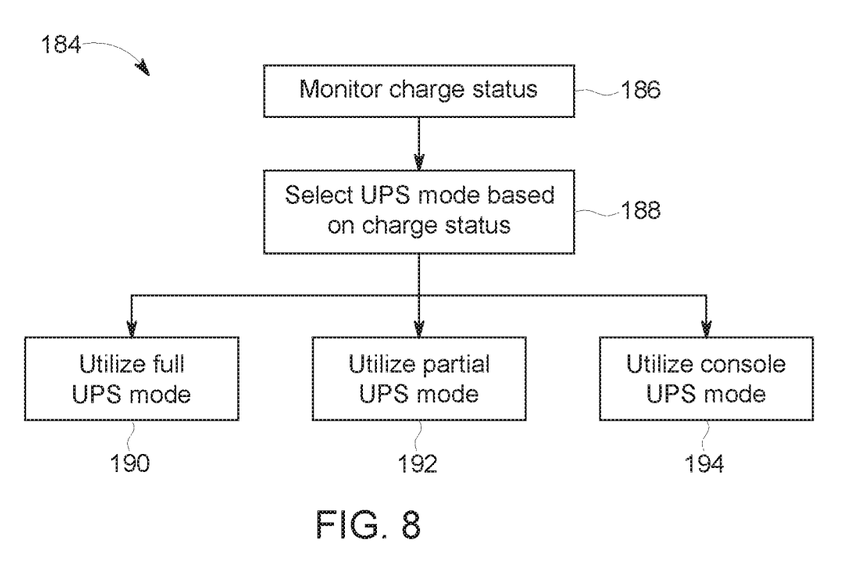
FIG. 8 is a flow diagram of an embodiment of a method for managing the utilization of power from an energy storage system (e.g., to determine UPS mode)

FIG. 8 is a flow diagram of an embodiment of a method 184 for managing the utilization of power from an energy storage system (e.g., to determine UPS mode) of the PDU 56. One or more steps of the method 184 may be performed by the energy storage management system 60 (e.g., control circuitry 78) and/or the control system 66. One or more of the steps of the method 184 may be performed in a different order as depicted in FIG. 8 and/or performed simultaneously. The method 184 includes monitoring a charge status of a battery (or batteries) of an energy storage component (e.g., utilized for the UPS and/or peak shaving) of the PDU 56 (block 186). The method 184 includes selecting a UPS mode (to determine how much of the operation to backup) during operation of the CT system 10 (e.g., during peak power operation) based on the charge status (block 188). It should be noted that in certain embodiments, a different parameter may be utilized to select the UPS mode. For example, a type of scan (trauma scan, body part being imaged, etc.) or timing based scheme (e.g., during different times of an operation of the CT system utilizing different UPS modes) may be utilized to select the UPS mode. Each UPS mode may represent a different percentage of power provided to the CT scanning apparatus by the energy storage component (e.g., during peak power operation). For example, the UPS modes may include a full UPS mode (e.g., batteries provide all of the power to the CT scanning apparatus during peak power operation), a partial UPS mode (e.g., batteries provide power only to a portion of the peak power operation that does not involve generating X-rays from the X-ray source 14), and a console UPS mode (e.g., batteries provide power only to the other system electronics 54 (e.g., operator console 40, computer 36, etc.)). The full UPS mode would utilize more power (e.g., 100 percent) from the energy storage component than the partial and console UPS modes, while the partial UPS mode would utilize more power than console UPS mode (e.g., 10 percent and 5 percent, respectively). The method 184 includes utilizing the full UPS mode (e.g., during peak power operation) if selected (block 190). The method 184 includes utilizing the partial UPS mode if selected (block 192). The method 184 includes utilizing the console UPS mode if selected (block 194).

Figure 9:
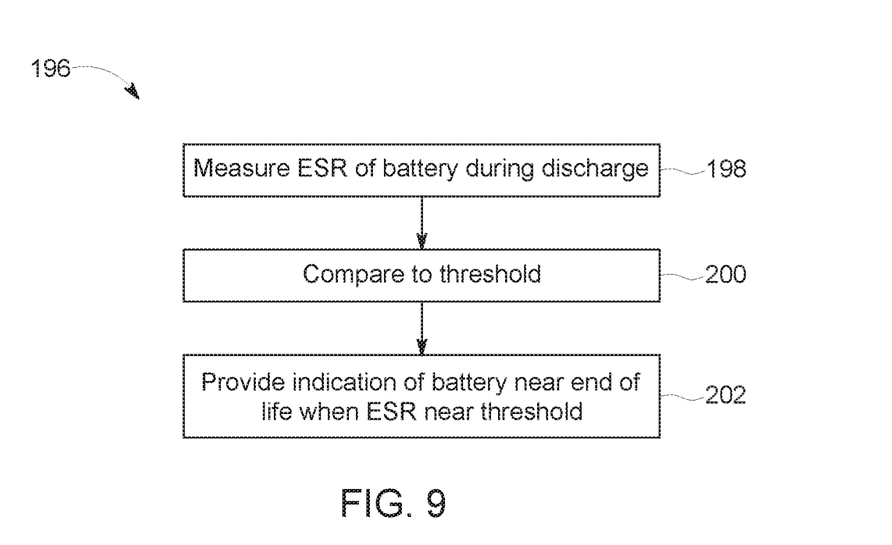
FIG. 9 is a flow diagram of an embodiment of a method for monitoring a life of a battery of an energy storage system.

FIG. 9 is a flow diagram of an embodiment of a method 196 for monitoring a life of a battery of an energy storage system of the PDU 56. One or more steps of the method 196 may be performed by the energy storage management system 60 (e.g., control circuitry 78) and/or the control system 66. One or more of the steps of the method 196 may be performed in a different order as depicted in FIG. 8 and/or performed simultaneously. The method 196 includes measuring an equivalent series resistance (ESR) of the battery or batteries of the energy storage system during discharge (block 198). In certain embodiments, a different parameter of battery like open battery voltage, charge voltage, charge current, or coulomb count may be utilized to determine life or charge status or percentage of charge of the battery or batteries. The method 196 also includes comparing the measured ESR to a threshold (e.g., representing a maximum allowed ESR value) (block 200). The method 196 further includes providing a user perceptible indication that the battery or batteries of the energy storage system is approaching (e.g., within a certain percentage such as 5 percent, 1 percent, etc.) the threshold and nearing the end of life (block 202).

Figure 10:
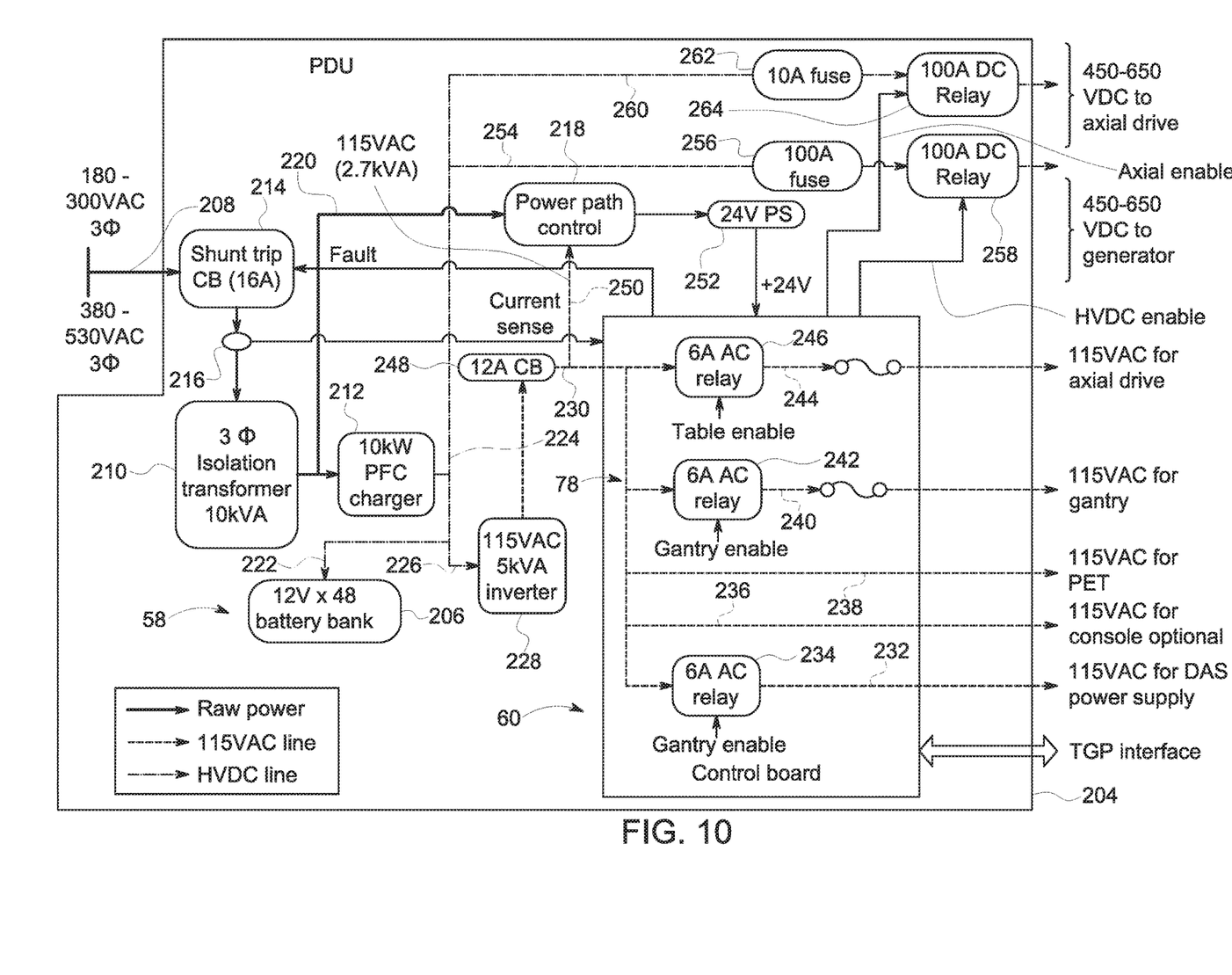
FIG. 10 is a schematic diagram of an embodiment of a PDU for a PET or CT/PET imaging system.

A similar PDU architecture can be utilized an imaging system that typically operates utilizing more power (e.g., 80 kVA or more or any higher power) than a typical CT system such as a PET or CT/PET imaging system. Techniques (e.g., such as utilizing a UPS for backup power and peak shaving) may be utilized to reduce the power requirements of these imaging systems. FIG. 10 is a schematic diagram of an embodiment of a PDU 204 for a PET or CT/PET imaging system. In general, the PDU 204 is similar to the PDU 56 in FIG. 4. The PDU 204 includes the energy storage system 58 and the energy storage management system 60. The energy storage system 58 includes the single energy storage component 206 that includes a plurality of batteries stacked in series. The stacking of the batteries in series avoids needing a pre-regulator. Although the number of batteries is depicted as 48, the number may vary so as long as the need for a pre-regulator is avoided. As described in greater detail below, the PDU 204 utilizes the energy storage component 206 for peak shaving (e.g., during peak power operation of the imaging system) and to provide power (e.g., backup power) during operation of the imaging system (e.g., peak power operation). The energy storage management system 60 includes control circuitry 78 that manages the distribution of power from the energy storage component 206 of the energy storage system 58. In certain embodiments, the energy storage management system 60 interfaces with a TGP.

As depicted, the PDU 204 is coupled to a three-phase AC power source via line 208 that provides electrical power to the isolation transformer 210 (e.g., 10 kVA isolation transformer). In certain embodiments, the PDU 204 could be coupled to a single-phase power suppl. The isolation transformer 210 provides power to the charger 212 (e.g., 10 kW power factor correction charger). A shunt trip circuit breaker 214 may be disposed along the line 208 upstream of the transformer 210 and charger 212. The shunt trip circuit breaker 214 trips in the presence of a fault. In certain embodiments, a current sensor 216 may be disposed along the line 208 (e.g., between the shunt trip circuit breaker 214 and the isolation transformer 210). The isolation transformer 210 provides power to a power path control 218 via portion 220 of line 208.

The charger 212 provides DC power along portion 222 of line 224 to the batteries 206. The charger 212 also provides via portion 226 of line 224 DC power to an inverter 228 (e.g., 115 VAC/5 kVA inverter) that converts the DC power to AC power that is provided to the energy storage management system 60. In particular, AC power (e.g., 2.7 kVA) may be provided via line 230 (e.g., 115 VAC line) to the energy storage management system 60. In certain embodiments, the inverter 228 may include a single-phase or polyphase output configuration when needed. From energy storage management system 60, the AC power may be provided via portion 232 of line 230 to a power supply for a DAS. In certain embodiments, an AC relay 234 may be disposed along portion 232 of line 230 downstream of the inverter 228. The AC relay 234 is turned on (e.g., gantry enabled) when the gantry 12 is being utilized. The AC power is also provided to other system electronics (e.g., computer, console, etc.) along portion 236 of line 230. AC power is provided for PET along portion 238 of line 230. Also, AC power is provided to the gantry along portion 240 of line 230. An AC relay 242 may be disposed along portion 240 that is turned on (e.g., gantry enabled) when the gantry is being utilized. Further, AC power is provided to the axial drive and motor along portion 244 of line 230. An AC relay 246 may be disposed along portion 244 that is turned on (e.g., axial drive enabled) when the axial drive and motor is being utilized. In certain embodiments, upstream of portions 232, 236, 238, 240, 244 and downstream of the inverter 228, a circuit breaker 248 may be disposed along the line 230. Downstream of the circuit breaker 248 and upstream of AC relay 246, AC power may be provided to the power path control 218 via portion 250 of line 230. The power path control 218 provides AC power to a power supply 252 (e.g., 24 V power supply) which provides power to the energy storage management system 60.

The charger 212 and/or batteries 206 provide DC power (e.g., 450-650 VDC) to the generator along portion 254 of line 224 (HVDC line). In certain embodiments, a fuse 256 and a DC relay 258 may be disposed (e.g., downstream of the batteries 206 and the battery charger 212) along the portion 254 of line 224. The DC relay 258 is turned on (e.g., HVDC enabled) when high voltage DC power is provided to the generator. In addition, the charger 212 and/or batteries 206 provide DC power (e.g., 450-650 VDC) to the axial drive and motor along portion 260 of line 224 (HVDC line). In certain embodiments, a fuse 262 and a DC relay 264 may be disposed (e.g., downstream of the batteries 206 and the battery charger 212) along the portion 260 of line 224. The DC relay 264 is turned on (e.g., axial enabled) when high voltage DC power is provided to the axial drive and motor.

Technical effects of the disclosed embodiments include providing a PDU for an imaging system that reduces the power requirements of the imaging system (e.g., during peak power operation). For example, an energy storage component of the PDU may be utilized for peak shaving (e.g., during peak power operation). Also, a UPS (e.g., disposed within a stationary portion of the imaging system to reduce the footprint of the system) may to be utilized for providing power (e.g., backup power). Besides reducing the power requirements of the imaging system, the disclosed embodiments of the PDU may enable the imaging system to be utilized with single phase AC power sources so the imaging system may be utilized in locations where three-phase AC power is inaccessible. Also, costs associated with utilization of the imaging system may be reduced (e.g., associated with power infrastructure, running costs, etc.).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computed tomography (CT) scanning apparatus, comprising:
   an energy storage component disposed in a stationary portion of the CT scanning apparatus, wherein the energy storage component is configured to receive electrical power from an external source and to store the electrical power; and
   an energy storage management system coupled to the energy storage component and configured to regulate both storage of the electrical power on the energy storage component and utilization of the electrical power stored on the energy storage component by the CT scanning apparatus, wherein the energy storage management system comprises a battery charger, a wide range stabilizer, and control circuitry;

wherein the energy storage component is configured to serve as an uninterruptible power supply (UPS) for the CT scanning apparatus and to provide peak power shaving during peak power operation of the CT scanning apparatus; and wherein, during an imaging operation by the CT scanning apparatus, the control circuitry is configured to turn off power provided to the battery charger during acceleration of a gantry of the CT scanning apparatus and to subsequently turn on power to the battery charger during emission of X-rays from an X-ray source of the CT scanning apparatus.

2. A computed tomography (CT) scanning apparatus, comprising:

an energy storage component disposed in a stationary portion of the CT scanning apparatus, wherein the energy storage component is configured to receive electrical power from an external source and to store the electrical power; and an energy storage management system coupled to the energy storage component and configured to regulate both storage of the electrical power on the energy storage component and utilization of the electrical power stored on the energy storage component by the CT scanning apparatus, and wherein the energy storage component comprises a plurality of batteries stacked in series and control circuitry;

wherein the energy storage component is configured to serve as an uninterruptible power supply (UPS) for the CT scanning apparatus and to provide peak power shaving during peak power operation of the CT scanning apparatus; and wherein the control circuitry is configured to select a UPS mode of operation from among a plurality of UPS modes of operation for the plurality of batteries during the peak power operation of the CT scanning apparatus, and wherein each UPS mode of operation represents a different percentage of the electrical power provided to the CT scanning apparatus by the plurality of batteries during the peak power operation.

3. The CT scanning apparatus of claim 2, wherein the electrical power provided by the external source to the energy storage component is a single-phase or polyphase alternating current.

* * * * *